United States Patent
Neetz

(10) Patent No.: US 10,127,663 B2
(45) Date of Patent: Nov. 13, 2018

(54) METHOD FOR CREATING A PRODUCTION MODEL FOR A PATIENT-SPECIFIC MEDICAL OBJECT

(71) Applicant: Siemens Healthcare GmbH, Erlangen (DE)

(72) Inventor: Manuel Neetz, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 107 days.

(21) Appl. No.: 15/171,010

(22) Filed: Jun. 2, 2016

(65) Prior Publication Data

US 2016/0371838 A1 Dec. 22, 2016

(30) Foreign Application Priority Data

Jun. 16, 2015 (DE) .................. 10 2015 211 047

(51) Int. Cl.
  *G06K 9/00* (2006.01)
  *G06T 7/00* (2017.01)
  *A61B 34/10* (2016.01)

(52) U.S. Cl.
  CPC ............ *G06T 7/0014* (2013.01); *A61B 34/10* (2016.02); *A61B 2034/102* (2016.02);
  (Continued)

(58) Field of Classification Search
  None
  See application file for complete search history.

(56) References Cited

U.S. PATENT DOCUMENTS

| 6,932,842 B1 | 8/2005 | Litschko et al. |
| 2009/0162813 A1 | 6/2009 | Glor et al. |

(Continued)

FOREIGN PATENT DOCUMENTS

| CN | 1350667 | 5/2002 |
| CN | 101257858 | 9/2008 |

(Continued)

OTHER PUBLICATIONS

Bagaria Vaibhav et al: "Use of rapid prototyping and three-dimensional reconstruction modeling in the management of complex fractures"; European Journal of Radiology 2011; 80. Jg. Nr. 3; pp. 814-820; 2011.

(Continued)

*Primary Examiner* — Nancy Bitar
(74) *Attorney, Agent, or Firm* — Harness, Dickey & Pierce, P.L.C.

(57) ABSTRACT

A method is disclosed for creating a production model for a patient-specific medical object. Image data relating to a body region are segmented into regions, each region corresponding with structures of different tissue. By way of the regions that correspond with the structures, a number of shape features is determined for the medical object. The shape features are compared with shape data relating to a plurality of stored object data sets. On the basis of the comparison of the shape features with the shape data, a prototype of the medical object is specified. The prototype of the medical object is defined as a production model. The production model is stored on a data carrier and/or output via an interface.

26 Claims, 4 Drawing Sheets

(52) U.S. Cl.
CPC .................. *A61B 2034/108* (2016.02); *G06T 2207/10081* (2013.01); *G06T 2207/10088* (2013.01); *G06T 2207/30012* (2013.01); *G06T 2207/30196* (2013.01)

(56) References Cited

U.S. PATENT DOCUMENTS

| | | | |
|---|---|---|---|
| 2011/0093108 A1 | 4/2011 | Ashby et al. | |
| 2011/0151400 A1* | 6/2011 | Boiangiu | A61F 2/2803 433/76 |
| 2012/0100500 A1* | 4/2012 | Gao | A61C 1/084 433/72 |
| 2012/0308843 A1* | 12/2012 | Ott | B23K 1/0018 428/614 |
| 2013/0203031 A1 | 8/2013 | McKinnon et al. | |
| 2013/0308843 A1* | 11/2013 | Tank | A61C 19/04 382/128 |
| 2015/0178925 A1* | 6/2015 | Jo | G06T 7/344 382/131 |
| 2016/0231732 A1* | 8/2016 | Neetz | G06F 19/321 |

FOREIGN PATENT DOCUMENTS

| | | |
|---|---|---|
| CN | 101969876 | 2/2011 |
| CN | 103153239 | 6/2013 |
| DE | 102006047054 A1 | 4/2008 |
| WO | WO 2004110309 A2 | 12/2004 |
| WO | WO 2014036551 A1 | 3/2014 |

OTHER PUBLICATIONS

Office Action dated Jun. 15, 2018 in Chinese Patent Application No. 2016104254383.

* cited by examiner

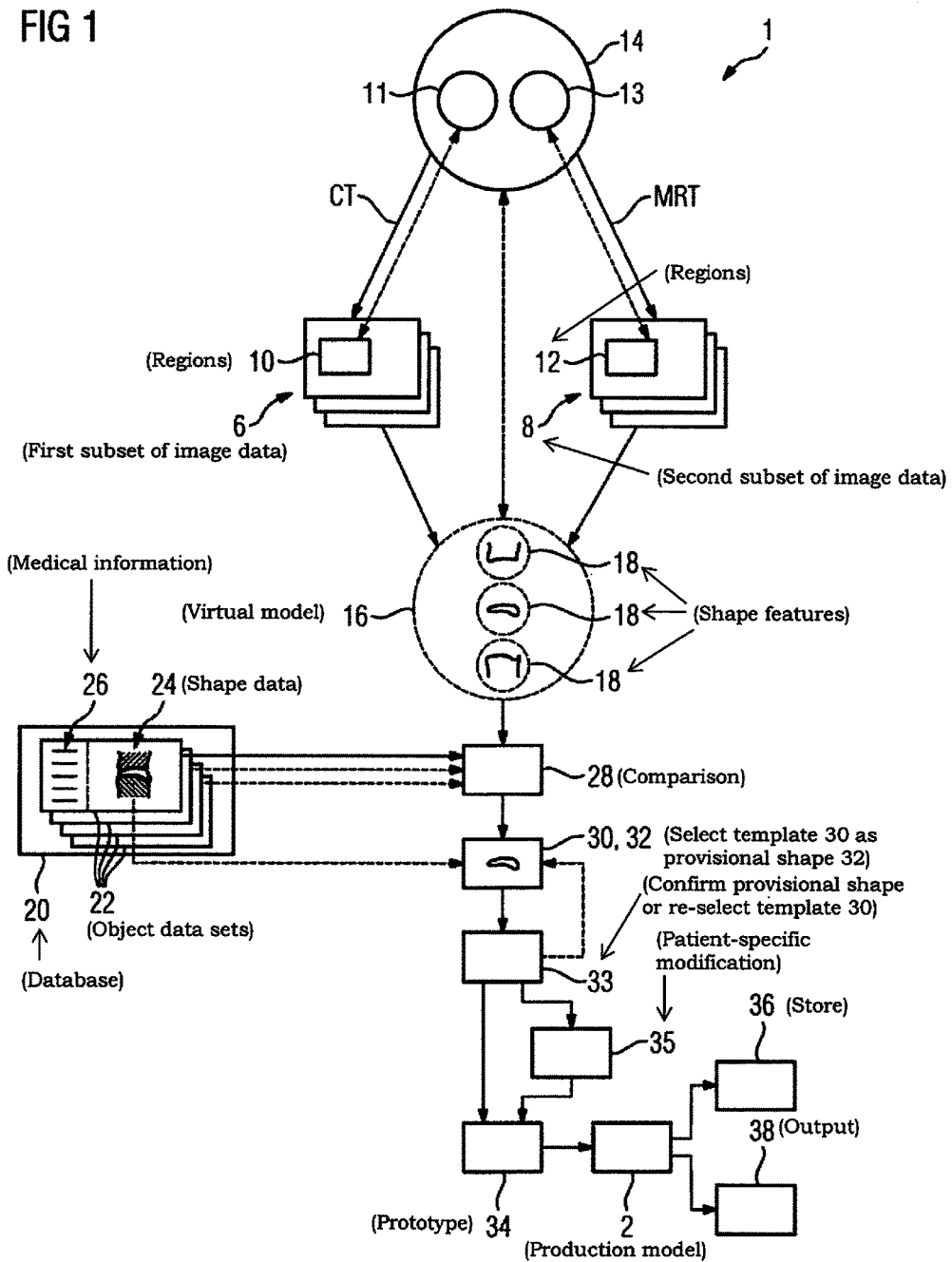

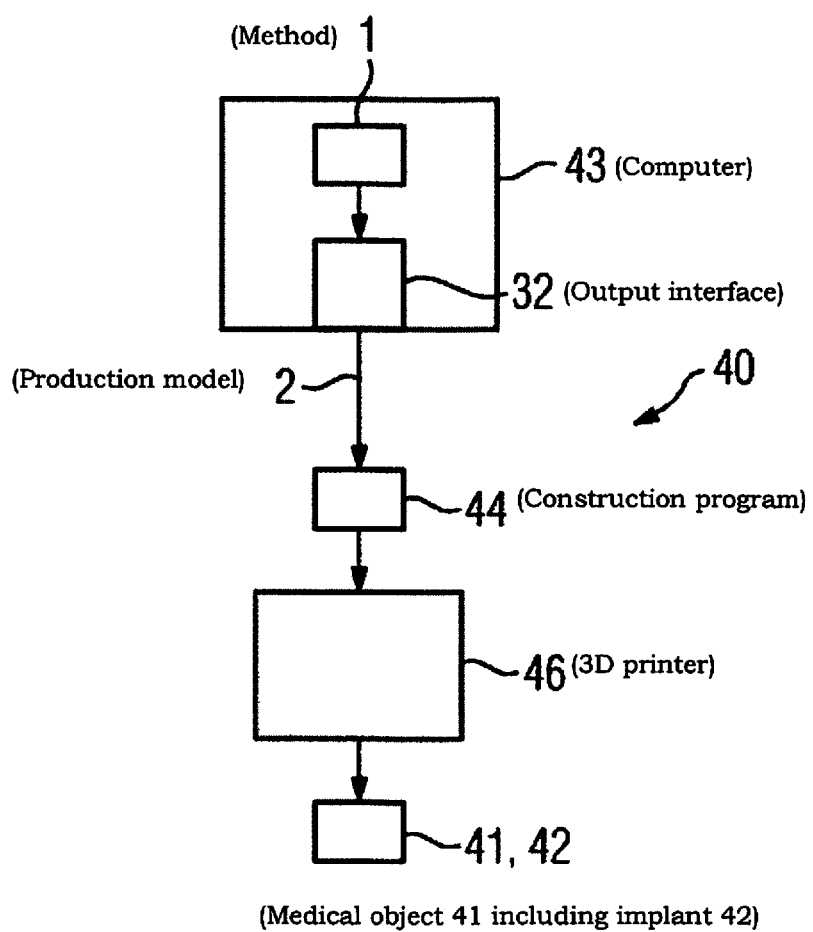

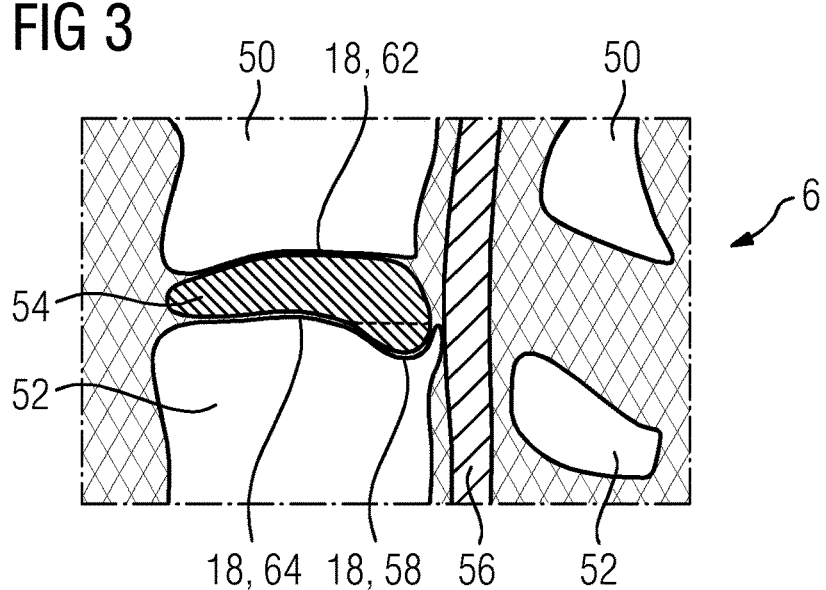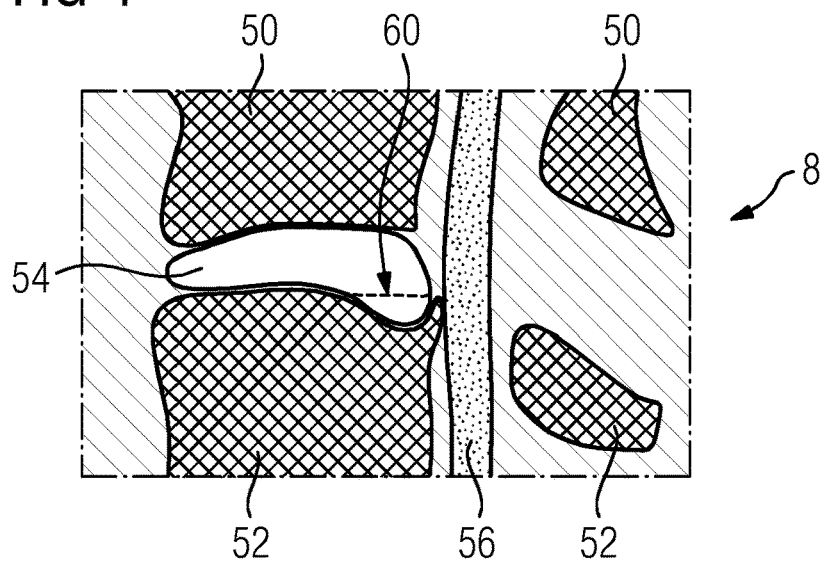

METHOD FOR CREATING A PRODUCTION MODEL FOR A PATIENT-SPECIFIC MEDICAL OBJECT

PRIORITY STATEMENT

The present application hereby claims priority under 35 U.S.C. § 119 to German patent application number DE 102015211047.8 filed Jun. 16, 2015, the entire contents of which are hereby incorporated herein by reference.

FIELD

At least one embodiment of the invention generally relates to a method for the creation of a production model for a patient-specific medical object, wherein image data relating to a body region is prepared, regions are segmented in the image data, which regions in each case correspond with structures of different tissue, and wherein a shape of the implant is defined by way of the regions corresponding with the structures.

BACKGROUND

It is desirable for the production of a medical implant or implantation aid to have as high as possible a degree of automation for high efficiency and yet to achieve as good an alignment as possible with the individual circumstances of the anatomy of the respective patient, which a priori creates an obstacle to a complete automation of production. The desire for a patient-specific anatomical alignment applies in such scenarios to such different implants as bone implants, a disk replacement or cartilage structures for plastic or reconstructive surgery.

Here, a detailed patient-specific alignment of the implant with surrounding tissue structures can prevent an inadequate integration of the implant into the tissue and consequently wear of the implant due to stresses resulting therefrom. Likewise, undesirable repercussions caused by the implant on the tissue structures participating in the interaction can be reduced, which helps to prevent inflammation, abrasion, concretion and physical wear reactions resulting from the implant.

A method is known from DE 10 2006 047 054 A1 by which implant mounts for the jaw region can be produced in a patient-individual manner. Here, a patient data set is first acquired from three-dimensional images from the affected jaw section and planning of the implant mount is carried out on the basis of the patient data set. The planning is subsequently converted into a planning data set, which is transmitted to a computer-controlled production method, a 3D-printing process, for example, for final production of the implant mount.

Such patient-specific production of a medical implant or of a comparable medical object by way of a patient data set from three-dimensional image data is first complex because a separate planning process needs to be carried out for each object that is to be produced on the basis of the image data. In addition to this, it is only the image data that is available for planning the object and usually not any further medical information. However, specifically for implants, spatial resolution alone of the body region in which the implant is to be inserted, without additional medical data relating to a healing process etc., for example, is often not sufficiently conclusive for a complete integration of the implant and a positive progression in the healing of the patient. Here, intensive aftercare may lead to further costs for the physician carrying out the follow-up treatment.

SUMMARY

The inventor has recognized that one problem is the providing of a method for creating a production model for a patient-specific medical object, which facilitates an optimum alignment of the implant with the patient-specific anatomical circumstances of the tissue structures surrounding the implant and at the same time allows optimum production efficiency.

At least one embodiment includes a method for creating a production model for a patient-specific medical object, wherein image data related to a body region is provided, regions are segmented in the image data, which regions in each case correspond with structures of different tissue, a number of shape features are defined for the medical object by way of the regions corresponding with the structures, the shape features are compared with shape data relating to a plurality of stored data sets, based on the comparison of the shape features with a prototype of the medical object, and the prototype of the medical object is defined as the production model, and the production model is stored on the data carrier and/or is output via an interface. Advantageous variants of the invention, which are partly inventive per se, are set out in the dependent claims in the description that follows.

A patient-specific medical object is to be understood in particular as an implant and an implantation or positioning aid for an implant. In at least one embodiment, the method can be carried out by a computer that comprises a data link with a data carrier and/or an interface. It is preferable in this case to provide image data relating to a body region for which the medical object is intended. In particular, the image data may also represent the body region in a time-resolved manner, for example a dynamic representation of a heart movement, if for instance the medical object is to be provided as a supporting structure in a coronary vessel or as a heart valve.

In an advantageous embodiment of the invention, image data is provided by at least two medical imaging methods each having a different modality, wherein a set of first image data is generated by a first modality and a set of second image data is generated by a second modality. In particular, the at least two medical imaging methods each have a different resolution with regard to various structures of different body tissue, such that in particular the first image data provides a particularly high resolution for at least a number of first structures, and the second image data provides particularly high resolution for at least a number of second structures. The quality of the resolution can be provided, for example, by the signal-noise ratio or the image contrast.

At least one embodiment of the invention further discloses an apparatus that is equipped to carry out at least one embodiment of the aforementioned method for creating a production model. This includes in particular a data processor or computer that can be equipped in particular with at least one ASIC designated for this purpose. The advantages listed for embodiments of the method and further developments thereof can be applied by analogy to the apparatus.

At least one embodiment of the invention further discloses a computer program with a programming code for the implementation of the aforementioned method for creating a production model when the computer program is run on a computer.

At least one embodiment of the invention further discloses a method for the production of a medical object, the process steps whereof include first the creation of a production model by way of a method described in the aforementioned, second the creation, by way of the production model, of a construction program that is readable by a production apparatus, and third the creation of the medical object in the production apparatus using the construction program, and likewise a patient-specific medical object, which has been manufactured by such a method. A particular advantage here is that the production model can be output by the method for the creation thereof in a data format that comprises a matrix-valued three-dimensional volume image of the implant, such as a CAD file, for example.

BRIEF DESCRIPTION OF THE DRAWINGS

An embodiment of the invention is described in further detail hereinafter by way of drawings. The drawings show a schematic view in each case of:

FIG. 1 a block diagram showing the flow chart for a method for creating a production model for a medical implant, FIG. 2 a block diagram showing the flow chart for a method for the production of a medical implant designed according to FIG. 1

FIG. 3 first image data relating to a body region of a spinal column,

FIG. 4 second image data relating to a body region of a spinal column,

DETAILED DESCRIPTION OF THE EXAMPLE EMBODIMENTS

Figure 5:
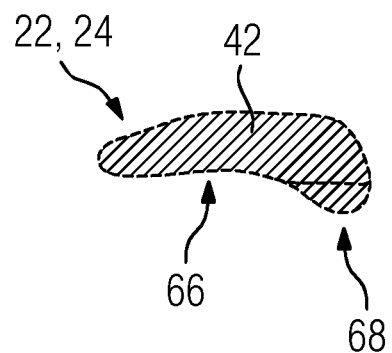
FIG. 5 shape data from an object data set that corresponds with the shape features of the spinal column according to FIG. 3 and FIG. 4, and FIG. 6 a spatial distribution of material properties of an implant according to FIG. 5.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the non-computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment includes a method for creating a production model for a patient-specific medical object, wherein image data related to a body region is provided, regions are segmented in the image data, which regions in each case correspond with structures of different tissue, a number of shape features are defined for the medical object by way of the regions corresponding with the structures, the shape features are compared with shape data relating to a plurality of stored data sets, based on the comparison of the shape features with a prototype of the medical object, and the prototype of the medical object is defined as the production model, and the production model is stored on the data carrier and/or is output via an interface. Advantageous variants of the invention, which are partly inventive per se, are set out in the dependent claims in the description that follows.

A patient-specific medical object is to be understood in particular as an implant and an implantation or positioning aid for an implant. In at least one embodiment, the method can be carried out by a computer that comprises a data link with a data carrier and/or an interface. It is preferable in this case to provide image data relating to a body region for which the medical object is intended. In particular, the image data may also represent the body region in a time-resolved manner, for example a dynamic representation of a heart movement, if for instance the medical object is to be provided as a supporting structure in a coronary vessel or as a heart valve.

For the segmentation, it is possible to consult landmarks, which in particular can also be set manually. The segmentation can also be supported by learning algorithms, such that, for example, a classification of the image data into regions with known patterns occurs for the segmentation, and regions that initially fail to correspond with a known pattern are classified manually, wherein the pattern recognition "learns" the relevant classification.

The shape features can be defined here, for example, as a negative shape with respect to the surface of a structure that corresponds to a segmented region. For this purpose, in particular the surface of the structure that corresponds with a region segmented in the image data can be calculated. In particular for identifying the shape features in the image data, regions can be identified that correspond with delineating structures that, for example, in a case where the medical object includes an implant, adjoin this after the implantation. For this purpose, the shape features can relate, for example, to a nature of the surface, the volume and/or the spatial expanse of recesses in a surface, which are intended to be filled or, however, to the angles of the structures with one another. To determine the shape features, landmarks can also be consulted, which in particular can also be set manually.

At the same time, at least one embodiment of the invention takes as its point of departure the consideration that a non patient-specific alignment of a medical object, such as for example, of an implant or an implantation aid with the individual anatomical circumstances of a body region, is most likely to be implemented by consulting image data related to the relevant body region of the patient. It is acknowledged here that the spatial resolution of the body region, which is available via the image data, can be used directly for the definition of a shape of the medical object, if regions in the image data that correspond in each case with structures of different tissues can be segmented. Through the segmentation of the individual regions, a model of the body region can be drawn up, which allows a definition of the shape of the medical object by assigning individual pixels to location information related thereto in a region intended for the medical object. Through a definition of this kind of the geometry of the medical object via the location information about pixels from image data, a shape can additionally be translated easily as a production model into a data format, which is directly readable for a production machine, so that it can directly produce the implant.

In a further step in at least one embodiment, it is now realized that the determination of a shape for the medical object can be carried out not only based on the image data or that an alignment of a shape can be acquired on the basis of the image data, but that for the medical object, which can find use in a plurality of patient treatments, each in a shape that is similar yet possibly modified in a patient-specific manner, it is possible to make a comparison with data for other specimens of the medical object that have the same identity.

For this purpose, shape features for the medical object are acquired on the basis of the regions corresponding with the structures. These shape features are compared with shape data from object data sets that can be stored in a database. The shape data is data that corresponds with the shape features of the patient-specific object, such as, for example, surface geometries, expanses, volumes, or even local angles between a patient-specific object and a contiguous structure in the relevant body region. The object data sets preferably need to be arranged in this case according to objects with the same identity as that of the medical object, that is, for example, "vertebra" or "disk".

In this case, an object data set can describe a concrete medical object in its shape data and optionally by further information such as those designed patient-specifically for a previous medical application and used as an implant, for example. The object data sets are consequently linked in each case with shape data for an object that has the same identity as that of the medical object that is intended to be produced. With the comparison, therefore, a link can be made with the shape data stored in the database for each respective case, wherein the shape data relating to a stored object can additionally be supplemented with further medical information.

As a result thereof, first the determination of a shape for the medical object is accelerated and simplified in order to generate a production model, since on the one hand no conclusive shape prototype can be acquired from the segmented regions in the image data, but it is sufficient to identify the shape features that are required for the comparison with the shape data stored in the object data sets. The geometrical data in the prototype, which is to be provided for the final production of the medical object in an adequate resolution, consequently does not have to acquired directly from the image data, but can be taken from already existing shape data in the stored object data sets, wherein the selection can ensue by way of the image data in a patient-specific manner.

In addition to this, for the selection of a shape, information stored in the object data sets can additionally be consulted, which data can likewise take into account, for example, treatment progressions or medical complications. Such information would otherwise not be available when planning the medical object. In order to make this information useful, an actual treatment scenario provided by the use of a medical object with the same identity as the object that is to be produced, is compared with the present medical situation as objectively and efficiently as possible, which is in fact achieved through the identification of the shape features in the present situation and by a comparison thereof with the shape data in the stored data sets.

Moreover, the stored shape data can additionally be calculated by machine learning, wherein the input data for the learning process can be based both on clinical cases and on numerical simulations. The database comprising the object data sets can be stored locally and designed to be updatable via a network or be designed as central data management such that a "cloud" can be activated via a "client".

It proves to be advantageous if a model of the body region shown can be produced from the segmented regions of the image data. Here, the segmented regions correspond with the structures of different tissue. The model is in particular a data model of the body region shown, which is consulted to determine the shape features of the structures. For this purpose, a model of the body region shown in the image data using information that is as comprehensive as possible may be particularly suitable since consequently not only shape parameters of the structures per se, but also optionally interactions of the structures with one another, for example, pressures or stresses can be determined in a patient-specific manner. As a result thereof, it is possible to avoid disadvantages that result from standardized production models for the medical object such as force vectors that have not been optimally aligned in an implant, which would have repercussions on the surrounding tissue and consequently result in permanent stresses with corresponding consequences such as irritations or inflammations.

In an advantageous embodiment of the invention, image data is provided by at least two medical imaging methods each having a different modality, wherein a set of first image data is generated by a first modality and a set of second image data is generated by a second modality. In particular, the at least two medical imaging methods each have a different resolution with regard to various structures of different body tissue, such that in particular the first image data provides a particularly high resolution for at least a number of first structures, and the second image data provides particularly high resolution for at least a number of second structures. The quality of the resolution can be provided, for example, by the signal-noise ratio or the image contrast.

In at least one particular embodiment, the at least two medical imaging methods include here MRT and CT, such that the structures that have a high resolution in the MRT include soft tissues and the structures that have a high resolution in the CT include bone tissue. This is advantageous in order to be able to determine an integration of the medical object into the surrounding structures, which may be made up of different types of tissue.

Moreover, as a result thereof, there is information available for the creation of the production model about any damage to those structures that have a particularly good resolution in each case for the modality used, which can be advantageous for a healing process or also for a long-term use in the case of an implant as a medical object since, in the event of an inadequate alignment of the implant, possible damage in the tissue, such as attrition on bones, for example, can lead to wear on the implant itself and to inflammation in the surrounding tissue.

An expedient feature here is that a number of regions corresponding to structures are segmented in the first image data and a number of areas corresponding to structures are segmented in the second image data, wherein a model of the body region shown is created from the regions in the first image data and the regions in the second image data. By using image data from different modalities, the model of the body region can represent in particularly accurate detail the various structures of different tissue that are depicted with a high resolution in each case due to the different modalities. As a result thereof, the quality of the determination of the shape features can be improved.

Conveniently, a provisional shape is determined as a shape feature for the medical object. Depending on the type of medical object, such as, for example, in the case of an implant that has a homogeneous body, the shape may represent the central feature distinguishing it from other possible implants. In this case, it is advantageous to first select a provisional shape for the medical object, optionally checking it using further data available in the object data sets and optionally modifying the provisional shape as a function of this data, and when a satisfactory result is obtained, to issue it as a prototype of the medical object.

In an advantageous embodiment of the invention, the prototype of the medical object is defined, a predefined template being selected from the stored object data sets, and the template being modified in a patient-specific manner using the shape features. In particular, the template can be superimposed with a patient-specific data model of the respective body region and aligned using the segmented regions. An at least partially manual alignment that makes use of the graphic display on a screen is also included here.

The use of a predefined template that is aligned individually with the anatomy of the patient takes into account the fact that implants of the same type often deviate from a basic shape determined by the average anatomy by only a few percent (with respect to the total volume of the implant). However, these deviations are often crucial for the correct medical function of the implant in the patient's body region.

Moreover, the use of such a basic shape as a template and the adaptation thereof makes it possible to design the definition of the shape to be less computation-intensive since there now remains only the patient-specific deviations from the basic shape to be calculated and no longer the complete implant. Since the selection of the template can ensue, for example, via a simple pattern recognition, this makes it possible to restrict the computation-intensive part of the shape definition to only a small percentage of the volume of the implant.

In a further advantageous embodiment of the invention, stored medical information relating to previous implants can be consulted for the comparison of the shape features with the shape data for the stored object data sets. This additional information can include, for example, data relating to treatment and/or healing progressions in the event of an implantation of an implant with the shape predefined by the shape data and/or data about long-term after-effects. Precisely when planning implants, a complex interaction of the implant with its immediate surroundings in the relevant body region has to be taken into account. Even when using high-resolution image data for what is a priori an advantageous prototype of the implant judging by the shape, it often happens that even an experienced physician who is involved in the planning may not consider all the possible subsequent complications that may often arise only over a number of years as the result of sequences of movements and stresses. As early as the implant planning stage, the automated acquisition of such treatment-related statistical data may therefore help to improve the chances of successful treatment involving an implant.

It proves to be advantageous if, by way of the comparison of the shape features with the shape data from the stored object data sets, a prototype is proposed and the prototype that has been proposed is defined by a confirmation from a user as the prototype of the medical object. Here the suggestion can, in particular, be automated, that is, for example, ensue by way of a computer that has access to the object data sets. This interaction considerably simplifies the determination of the prototype since a user, a physician, for example, is placed before the simple, binary decision to either confirm a proposed, finished geometrical shape for the prototype on the basis of a diagnosis that has been made or to not accept it. On the other hand, there is in fact the option of rejecting the proposed prototype, and give a physician the opportunity of having incorporated into the determination of the prototype patient-individual additional information, in particular that for which there may be no adequate statistical data in existence regarding previous treatments.

Expediently, a geometrical combination of a plurality of shape data each from respective different stored object data sets is consulted for the determination of the prototype of the medical object. In the event that, depending on the region, a particularly good match of the shape features that have been determined is achieved in each case with the shape data for respective different object data sets, a combination of this shape data for the prototype of the medical object and ultimately for the production model can help to simplify and speed up the production process for the medical object, when depositing the relevant machine-readable construction data in the object data sets or when translating the shape data into machine-readable construction data.

For the prototype of the medical object, information about a spatial distribution of material properties and/or a density and/or surface properties is preferably taken into account. Here, surface properties also include an additional surface coating, with antibiotic effect for example, for implantation in an inflamed area. Information regarding a spatial distribution of the density or the material properties is advantageous in particular for the production of implants in which a non-homogeneous design may lead to a greater durability or to an improved treatment success for the patient. This is conceivable for disk implants or bone implants for example, where the stresses are not distributed equally across the implant as a whole.

At least one embodiment of the invention further discloses an apparatus that is equipped to carry out at least one embodiment of the aforementioned method for creating a production model. This includes in particular a data processor or computer that can be equipped in particular with at least one ASIC designated for this purpose. The advantages listed for embodiments of the method and further developments thereof can be applied by analogy to the apparatus.

At least one embodiment of the invention further discloses a computer program with a programming code for the implementation of the aforementioned method for creating a production model when the computer program is run on a computer.

At least one embodiment of the invention further discloses a method for the production of a medical object, the process steps whereof include first the creation of a production model by way of a method described in the aforementioned, second the creation, by way of the production model, of a construction program that is readable by a production apparatus, and third the creation of the medical object in the production apparatus using the construction program, and likewise a patient-specific medical object, which has been manufactured by such a method. A particular advantage here is that the production model can be output by the method for the creation thereof in a data format that comprises a matrix-valued three-dimensional volume image of the implant, such as a CAD file, for example.

Such an image can be translated for a plurality of production apparatus, such as for a 3D printer or a milling machine, for example, directly into a construction program that is readable by the apparatus. The program can include the instructions to the apparatus that are necessary for production, such as a file in the .stl format, for instance, in the case of a 3D printer. This guarantees a high viability and practical usability of the production model that is output. In particular, when the output takes the form of an advantageous file format, the creation of the production model can be separated from the physical production of the medical object, which may contribute to a simplification of production.

Components and values that correspond with one another are in each case denoted by the same reference signs in all the figures.

FIG. 1 shows in schematic form a block diagram for a method 1 for creating a production model 2 for a medical object, which in the present example is provided by an implant. In the present case, a set of first image data 6 and a set of second image data 8 are supplied by two medical imaging methods, CT, MRT, which are provided in this case by a computer tomography scan CT and a magnetic resonance tomography scan MRT. A different variant of the method 1, which is not shown here and in which image data is provided only by one medical imaging method, progresses in a similar manner. The first image data 6 and the second image data 8 are segmented separately from each other in each case. This means that in the individual image data, related regions 10, 12 are acquired on the basis of certain homogeneity criteria, which in each case depict structures 11, 13 of the same tissue. In the present case, the regions 10 that are segmented in the first image data 6 provided by the CT scan correspond with structures 11 of bone tissue, since this is shown with a particularly high resolution by the CT scan. The regions 12 that are segmented in the second image data 8 provided by the MRT scan accordingly depict structures 13 of soft tissue from the relevant body region 14.

From the regions 10 that are segmented in the first image data 6 and the regions 12 that are segmented in the second image data 8, a virtual model 16 of the body region depicted 14 is now established. By way of this model 16 and the segmented regions 10, 12 corresponding with the structures 11, 13, shape features 18 are now established which provide detailed geometrical information about the structures 11, 13 of the body region 14. These shape features can include, for example, surface geometries, distances, and angles in the structures. In a database 20, a number of object data sets 22 is stored. Each object data set 22 corresponds here with an implant that has already been implanted in a previous treatment of a different patient at the same place in the body as the implant for which the production model 2 is to be established in method 1, that is, a disk, for example. In each object data set 22, shape data 24 is stored relating to the respective implant used in practice, which data describes the geometry of the implant in high resolution. Furthermore, additional medical information 26 is stored regarding the implantation, the progression of treatment and possible subsequent complications, as well as, where applicable, further relevant information concerning the patient who is receiving the implant.

The shape features 18 acquired with respect to the structures 11, 13 of the body region 14 are now subjected to a comparison process 28 with the shape data 24 for the individual object data sets 22 stored in the database 20, wherein the additional medical information 26 can also be consulted for the comparison 28. On the basis of the comparison 28, a template 30 is now selected from the object data sets 22, which template acts as a provisional shape 32 for the production model 2. Here the template 30 is provided by the shape of an implant that can be defined on the basis of the shape data 24 in a concrete object data set 22. The provisional shape 32 can now be selected by a user, a physician for example, by confirmation 33 as the prototype 34 for the production model 2, or in addition to this can also be aligned using a patient-specific modification 35. In the event that the provisional shape 32 is rejected entirely, the method 1 suggests a new template 30 from a different object data set 22, which can now be confirmed and where necessary modified. The prototype 36 of the implant is established as the production model 2 for the implant and can now be stored on a data carrier 36 and output via an interface 38.

FIG. 2 shows in schematic form a block diagram for the sequence of a method 40 for the production of a medical object 41 designed according to FIG. 1. The medical object 41 includes an implant 42. According to the aforementioned method 1 that is illustrated in FIG. 1, a production model 2 for the implant 42 is created on a computer 43 designed specifically for this purpose and is output via an interface 32. The production model 2 is now translated into a construction program 44 that can be read directly by a production apparatus, provided here as a 3D printer 46, that is, for example in a file in the .stl-format. The 3D printer 46 now creates the implant 42 using the construction program 44, which represents a direct implementation of the production model 2.

FIG. 3 and FIG. 4 both show in schematic form the same longitudinal sectional plane of a section of a spine in first image data 6 and in second image data 8, which depict two vertebrae 50, 52 and a disk 54 located between them. In the first image data 6 shown in FIG. 3, the two vertebrae 50, 52 can be detected particularly well by the high contrast; in the second image data 8 shown in FIG. 4, the disk 54 and the spinal cord 56 behind it are shown with a better resolution. In the first image data a slight indentation 58 can be detected on the lower vertebra 52, which represents a slight deviation from the shape 60 that is usually to be expected for the same vertebra in the average person. This shape 60 that is usually to be expected is drawn with a dotted line for the sake of clarity and does not represent a component of the image data. The indentation 58 may be congenital or may have occurred as a result of incorrect posture over a number of years or of stress due to attrition. In the second image data 8, it is possible to detect that in the vicinity of the indentation 58 the spinal cord 56 runs past the vertebrae 50, 52. The surfaces 62, 64 of the vertebrae 50, 52 that border on the disk 54 and likewise in particular the indentation 58 are included here in the shape features 18 that are acquired from the image data 6 and 8 for the progression of the method 1 according to FIG. 1.

FIG. 5 shows in schematic form, in a longitudinal sectional view, the shape data 24 relating to an object data set 22 that correspond to the shape features 18 of the disk 54 that is shown in FIG. 3 and FIG. 4. The shape data 24 shows an implant 42 for a disk that has a protrusion 68 on the underside. Due to the protrusion 68, the underside 66 corresponds exactly with the negative shape of the surface 64 of the vertebra 52 shown in FIG. 3 and FIG. 4. An implant without this protrusion 68, which has a straight underside, the course of which corresponds with a course that corresponds with the shape 60 that is usually to be expected, is not consulted for the further progression of the method for creating a production model that is shown in FIG. 1.

Figure 6:
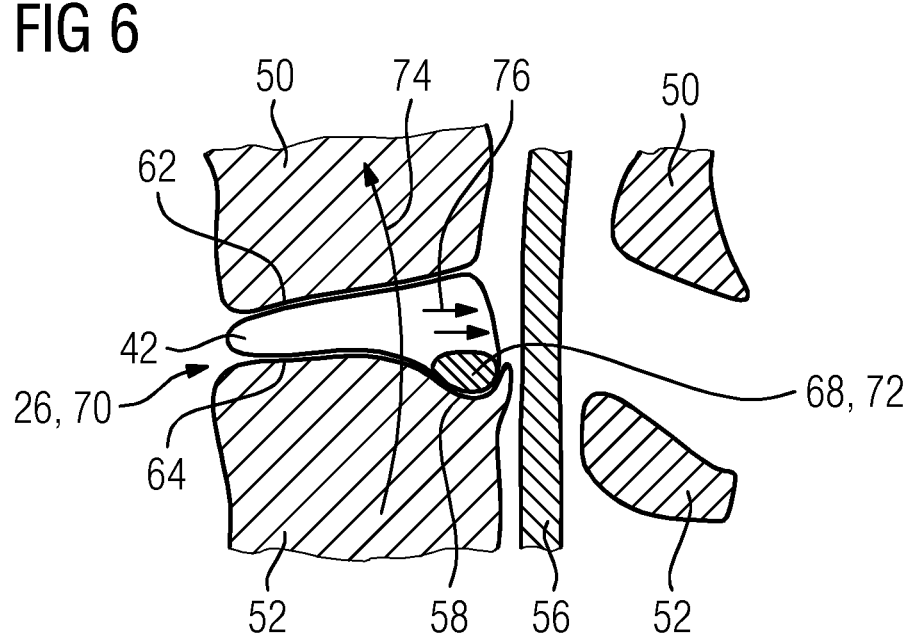

FIG. 6 shows in schematic form, in a longitudinal sectional view, a spatial distribution 70 of material properties in an implant 42 that can be stored together with additional medical information 26 in an object data set 22 according to FIG. 5 and is to be considered for the comparison with the shape features 18 according to FIG. 3 and FIG. 4. In the region of the protrusion 68, which complements the indentation 58 in the vertebra 52, the implant 42 comprises a reinforcement 72. Without this reinforcement 72, precisely in the event of a curvature 74 of the spine that leads to a wedge-shaped displacement of the surfaces 62, 64 with respect to each other, the implant 42 could be pushed to an excessive extent into the indentation 58 due to the forces 76 operating towards the spinal cord 56 as a result of the curvature 72 even with an optimum fit. This additional medical information 26 would not, however, be apparent from the image data alone 6, 8 according to FIG. 3 and FIG. 4 such that a production model which consults only the image data might possibly lead to a finished implant that could cause long-term complications as a result of slipping out of place. Such complications can be prevented through the reinforcement 74, which avoids the implant 42 slowly slipping out of place due to curvatures 74 of the spine.

Although the invention has been illustrated and described in greater detail with the preferred embodiment, the invention is not restricted by this embodiment. Other variants can be derived therefrom by a person skilled in the art without going beyond the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for defining a production model for a patient-specific medical object, the method comprising:
   segmenting image data relating to a body region of a patient into a plurality of regions, the image data including a first subset of image data generated by a first imaging method and a second subset of image data generated by a second imaging method, the plurality of regions corresponding with structures of different tissues in the body region of the patient, the segmenting segments the first subset of image data into a first plurality of regions and segments the second subset of image data into a second plurality of regions;
   generating a model of the body region based on the first plurality of regions and the second plurality of regions;
   determining one or more shape features corresponding to at least one of the plurality of regions based on the model of the body region;
   comparing the one or more shape features with at least one set of shape data relating to a plurality of stored templates;
   specifying a prototype of the patient-specific medical object by,
      selecting a template among the plurality of stored templates based on the comparing, and
      modifying the selected template to correspond to the body region of the patient based on the one or more shape features;

defining the production model based on the specified prototype of the patient-specific medical object; and
performing at least one of,
storing the defined production model on a data carrier, or
outputting the defined production model via an interface.

2. The method of claim 1, wherein the one or more shape features include a provisional shape.

3. The method of claim 1, wherein the comparing includes determining additional medical information regarding previous implants.

4. The method of claim 1, further comprising:
receiving a confirmation of the prototype.

5. The method of claim 1, wherein the comparing compares the one or more shape features with a combination of a plurality of sets of shape data.

6. The method of claim 1, wherein the specifying includes determining at least one of a spatial distribution of material properties or density and surface properties of the patient-specific medical object.

7. An apparatus for defining a production model for a patient-specific medical object, the apparatus comprising:
one or more processors configured to execute computer-readable instructions to,
segment image data relating to a body region of a patient into a plurality of regions including a first plurality of regions and a second plurality of regions, the image data including a first subset of image data generated by a first imaging method and a second subset of image data generated by a second imaging method, the plurality of regions corresponding with structures of different tissues in the body region of the patient, the segmentation segments the first subset of image data into the first plurality of regions and segments the second subset of image data into the second plurality of regions,
generate a model of the body region based on the first plurality of regions and the second plurality of regions,
determine one or more shape features corresponding to at least one of the plurality of regions based on the model of the body region,
compare the one or more shape features with at least one set of shape data relating to a plurality of stored templates,
specify a prototype of the patient-specific medical object by,
selecting a template among the plurality of stored templates based on the comparison, and
modifying the selected template to correspond to the body region of the patient based on the one or more shape features,
define the production model based on the specified prototype of the patient-specific medical object, and
perform at least one of,
control storing of the defined production model on a data carrier, or
control output of the defined production model via an interface.

8. A non-transitory computer readable medium storing programming code that, when executed by at least one processor, causes the at least one processor to perform the method of claim 1.

9. A method for creating a patient-specific medical object, the method comprising:
defining the production model via the method of claim 1;
creating a construction dataset readable by a production apparatus, based on the production model; and
creating the patient-specific medical object in the production apparatus based on the construction dataset.

10. A patient-specific medical object produced by the method of claim 9.

11. The method of claim 1, wherein the first and second imaging methods include computed tomography and medical resonance imaging.

12. The apparatus of claim 7, wherein the first and second imaging methods include computed tomography and medical resonance imaging.

13. The apparatus of claim 7, wherein the one or more shape features include a provisional shape.

14. The apparatus of claim 7, wherein the comparison includes determining additional medical information regarding previous implants.

15. The apparatus of claim 7, wherein the one or more processors are configured to execute the computer-readable instructions to receive a confirmation of the prototype.

16. The apparatus of claim 7, further comprising:
a memory storing the computer-readable instructions.

17. The apparatus of claim 7, further comprising:
at least one medical imaging device configured to generate the image data.

18. The apparatus of claim 17, wherein
the at least one medical imaging device includes a first medical imaging device configured to generate the first subset of image data and a second medical imaging device configured to generate the second subset of image data, the first medical imaging device and the second medical imaging device being different.

19. The apparatus of claim 16, further comprising:
at least one medical imaging device configured to generate the image data.

20. The apparatus of claim 19, wherein
the at least one medical imaging device includes a first medical imaging device configured to generate the first subset of image data and a second medical imaging device configured to generate the second subset of image data, the first medical imaging device and the second medical imaging device being different.

21. A non-transitory computer readable medium storing programming code that, when executed by at least one processor, causes the at least one processor to perform the method of claim 3.

22. A non-transitory computer readable medium storing programming code that, when executed by at least one processor, causes the at least one processor to perform the method of claim 6.

23. A method for creating a patient-specific medical object, the method comprising:
defining the production model via the method of claim 3;
creating a construction dataset readable by a production apparatus based on the production model; and
creating the patient-specific medical object in the production apparatus based on the construction dataset.

24. A patient-specific medical object produced by the method of claim 23.

25. A method for creating a patient-specific medical object, the method comprising:
defining the production model via the method of claim 6;
creating a construction dataset readable by a production apparatus based on the production model; and
creating the patient-specific medical object in the production apparatus based on the construction dataset.

26. A patient-specific medical object produced by the method of claim 25.

* * * * *